(12) United States Patent
Majeed et al.

(10) Patent No.: US 12,257,274 B2
(45) Date of Patent: *Mar. 25, 2025

(54) FRUCTOPHILIC LACTIC ACID PRODUCING BACTERIA

(71) Applicants: Muhammed Majeed, Bangalore (IN); Kalyanam Nagabhushanam, East Windsor, NJ (US); Kirankumar Beede, Bangalore (IN); Sivakumar Arumugam, Bangalore (IN)

(72) Inventors: Muhammed Majeed, Bangalore (IN); Kalyanam Nagabhushanam, East Windsor, NJ (US); Kirankumar Beede, Bangalore (IN); Sivakumar Arumugam, Bangalore (IN)

(73) Assignee: Sami-Sabinsa Group Limited, Bangalore (IN)

( * ) Notice: Subject to any disclaimer, the term of this patent is extended or adjusted under 35 U.S.C. 154(b) by 726 days.

This patent is subject to a terminal disclaimer.

(21) Appl. No.: 17/521,383

(22) Filed: Nov. 8, 2021

(65) Prior Publication Data
US 2022/0118032 A1    Apr. 21, 2022

Related U.S. Application Data

(63) Continuation-in-part of application No. 16/410,054, filed on May 13, 2019, now Pat. No. 11,197,898.

(51) Int. Cl.
| | |
|---|---|
| A61K 35/741 | (2015.01) |
| A61K 9/20 | (2006.01) |
| C12N 1/20 | (2006.01) |
| C12P 7/56 | (2006.01) |
| C12Q 1/689 | (2018.01) |
| C12R 1/07 | (2006.01) |

(52) U.S. Cl.
CPC .......... *A61K 35/741* (2013.01); *A61K 9/2054* (2013.01); *C12N 1/205* (2021.05); *C12P 7/56* (2013.01); *C12Q 1/689* (2013.01); *C12R 2001/07* (2021.05)

(58) Field of Classification Search
CPC .................................................... A61K 35/741
See application file for complete search history.

(56) References Cited

U.S. PATENT DOCUMENTS 11,197,898 B2 *   12/2021   Majeed .................... C12P 7/56

* cited by examiner

*Primary Examiner* — Albert M Navarro (57) ABSTRACT

The present invention discloses a novel fructophilic lactic acid producing bacteria *Bacillus coagulans* strain FF-7 (MTCC 25235) and the process of isolation and characterization of the bacteria.

7 Claims, 8 Drawing Sheets
(2 of 8 Drawing Sheet(s) Filed in Color)
Specification includes a Sequence Listing.

FRUCTOPHILIC LACTIC ACID PRODUCING BACTERIA

CROSS REFERENCE TO RELATED APPLICATION

This application is a continuation-in-part of U.S. application Ser. No. 16/410,054 filed on 13 May 2019, the contents of which is incorporated herein in its entirety.

BACKGROUND OF THE INVENTION

Field of the Invention

The invention in general relates to fructophilic lactic acid producing bacteria. More specifically, the present invention relates to isolation, characterization and biological applications of fructophilic probiotic bacteria *Bacillus coagulans*.

Description of Prior Art

Probiotics and its importance in health and prevention of many disorders have been already reported. Fructophilic lactic acid bacteria (FLAB) are a special group of lactic acid bacteria which utilizes fructose as a growth substrate. Due to their unique characteristics of poor growth on glucose and preference of oxygen, they are regarded as "unconventional" lactic acid bacteria (LAB). Their unusual growth characteristics are due to an incomplete gene encoding a bifunctional alcohol/acetaldehyde dehydrogenase (adhE). This results in the imbalance of NAD/NADH and the requirement of additional electron acceptors to metabolize glucose. Oxygen, fructose, and pyruvate are used as electron acceptors. FLAB have significantly fewer genes for carbohydrate metabolism than other LAB, especially due to the lack of complete phosphotransferase system (PTS) transporters. FLABs were originally classified as *Leuconostoc* species and later reclassified as *Fructobacillus* species based on their phylogenetic positions and biochemical and morphological characteristics. (Endo A, Okada S. 2008. Reclassification of the genus *Leuconostoc* and proposals of *Fructobacillus fructosus* gen. nov., comb. nov., *Fructobacillus durionis* comb. nov., *Fructobacillus ficulneus* comb. nov. and *Fructobacillus pseudoficulneus* comb. nov. Int J Syst Evol Microbiol 58:2195-2205).

The metabolism of fructose starts with the enzyme fructase in the liver. The fructose load is converted into lactate in enterocytes and in the liver. Further, excess fructose in the liver is directed toward peripheral tissues, and is taken up by the insulin-dependent glucose transporter, GLUT 4, present on adipose tissue is converted into fatty acids. GLUT 4 is reported to play an important role in the development of fructose-induced hepatic steatosis and dyslipidemia. Further, several fructose induced metabolic disorders are reported like NASH, NAFLD, Dyslipidemia, ectopic lipid deposition in the liver and skeletal muscle, Uric Acid Metabolism, High Blood Pressure, Mineral Metabolism. (Prasanthi Jegatheesan and Jean-Pascal De Bandt, Fructose and NAFLD: The Multifaceted Aspects of Fructose Metabolism, Nutrients. 2017 March; 9(3): 230; Bidwell A J, Chronic Fructose Ingestion as a Major Health Concern: Is a Sedentary Lifestyle Making It Worse? A Review, Nutrients. 2017 June; 9(6): 549). Excessive fructose intake is also associated with increased cardiovascular risk. Increase in fructose intake may also lead to lactic acidosis by excessively decreasing the pH in blood.

Probiotics play an important role in metabolizing intestinal fructose. The low dose of fructose that is orally consumed, reach the intestine and is metabolized in the presence of different enzymes and inherent microbiota. However, in the presence of high dose of fructose, the load of fructose spills over from intestine to liver. In order to reduce the spillover of fructose from intestine to liver, probiotics play an important role to convert fructose to SCFAs (Short chain fatty acids).

FLABs are isolated from various sources such as fruits and vegetables, human stool culture, natural antimicrobial agent, cheese, kefir grains, dairy and non-dairy products, fermented and raw milk, feces of breast fed infants, lactating milk, sheep, buffalo and cow milk, yogurt, beverages, poultry sources, animal rumen contents, Pengging Duck's caecum, chicken intestine and fecal samples, chicken feed, enzymes, fermented rice, curd, meat and yeast extracts, glucose and sucrose, human gut, human colonial epithelial cells, human and animal vagina and mouth extraction, diapers of human babies, pineapples wastes, industrial sausages, ice-cream, small intestines of piglets, corn slurry, crop and intestinal ducks. The following prior art documents describes the isolation of different FLABs.

1. Akihito Endo, Fructophilic lactic acid bacteria inhabit fructose-rich niches in nature, Microb Ecol Health Dis. 2012; 23
2. Akihito Endo, Shintaro Maeno, Yasuhiro Tanizawa, Wolfgang Kneifel, Masanori Arita, Leon Dicks, Seppo Salminen, Fructophilic Lactic Acid Bacteria, a Unique Group of Fructose Fermenting Microbes, Minireview, Applied and Environmental Microbiology, October 2018 Volume 84 Issue 19 e01290-18
3. Arshad F, Mehmood R, Hussain S, Khan M A, Khan M S (2018) Lactobacilli as Probiotics and their Isolation from Different Sources. Br J Res 5 (3): 43

Given that the biological effects of probiotics are strain specific and cannot be generalized to all strains and species (Guidelines for the evaluation of probiotics in food, Joint FAO/WHO Working Group Report on Drafting Guidelines for the Evaluation of Probiotics in Food, London, Ontario, Canada, Apr. 30 and May 1, 2002, See section 3.1 indicating that "The current state of evidence suggests that probiotic effects are strain specific. Strain identity is important to link a strain to a specific health effect as well as to enable accurate surveillance and epidemiological studies."), there still exists a need to find a superior fructophilic probiotic bacteria with improved biological functions. The present invention solves the above problem by disclosing a novel fructophilic lactic acid bacteria *Bacillus coagulans* MTCC 25235.

It is the principal objective of the invention to disclose a novel fructophilic lactic acid producing bacteria *Bacillus coagulans* MTCC 25235 and its process of isolation.

It is another objective of the invention to disclose the production of short chain fatty acid by fructophilic lactic acid producing bacteria *Bacillus coagulans* MTCC 25235.

It is yet another objective of the invention to disclose the anti-microbial effects of fructophilic lactic acid producing bacteria *Bacillus coagulans* MTCC 25235.

The present invention solves the above mentioned objectives and provides further related advantages.

DEPOSIT OF BIOLOGICAL MATERIAL

The deposit of biological material *Bacillus coagulans* strain FF7 bearing accession number MTCC 25235, mentioned in the instant application has been made on 28 Feb.

2019 at Microbial Type Culture Collection & Gene Bank (MTCC), CSIR-Institute of Microbial Technology, Sector 39-A, Chandigarh-160036, India.

SUMMARY OF THE INVENTION

The present invention discloses the fructophilic lactic acid producing bacteria. The invention further discloses the process of isolation, characterization and biological applications/therapeutic use of fructophilic lactic acid producing bacteria.

Other features and advantages of the present invention will become apparent from the following more detailed description, which illustrate, by way of example, the principle of the invention.

BRIEF DESCRIPTION OF DRAWINGS

The patent or application file contains at least one drawing executed in color. Copies of this patent or patent application publication with color drawing(s) will be provided by the office upon request and payment of the necessary fee.

FIGS. 8A and 8B shows BSH activity of *Bacillus coagulans* MTCC 25235.

FIGS. 12A, 12B and 12 C shows graphical presentation of Acetic FIG. 12A, butyric FIG. 12 B and propionic acid FIG. 12C production from the *Bacillus coagulans* MTCC 25235 while fermenting fructose, FOS, cranberry seed fiber, fenugreek seeds fiber. Samples were collected after 4, 8, 12, 18 and 24 h of fermentation. Values are average mean of triplicate performed at two different occasions and represented in mg/g.

DESCRIPTION OF THE MOST PREFERRED EMBODIMENTS

In the most preferred embodiment, the present invention discloses a method for isolating and identifying novel fructose utilizing probiotic bacteria from honey, comprising step of:

a) Mixing honey with saline in the ratio of 1:10 w/v to obtain a suspension;
b) Thoroughly mixing the suspension of step a) and providing heat shock at 50-70° C. for 30 minutes for selective isolation of spores;
c) Isolating the bacterial colonies by incubating 1-2 ml of the suspension from step b) in suitable culture media containing fructose for 48 hrs at 35-37° C.;
d) Purifying bacterial isolates by selecting and incubating morphologically distinct colonies in a suitable media containing fructose as carbon source;
e) Identifying the bacterial strain by biochemical analysis and 16S rRNA sequencing as *Bacillus coagulans* strain FF7 bearing accession no. MTCC 25235.

In a related aspect, the honey is selected from the group comprising, but not limited to, raw honey, filtered honey, acacia honey, alfalfa honey, aster honey, avocado honey, basswood honey, beechwood honey, blueberry honey, bluegum honey, buckwheat honey, clover honey, dandelion honey, *eucalyptus* honey, fireweed honey, heather honey, ironbark honey, jarrah honey, leatherwood honey, linden honey, macadamia honey, manuka honey, orangeblossom honey, pinetree honey, sourwood honey, sage honey, and tupelo honey. In another related aspect, the culture media is selected from the group comprising MRS (De Man, Rogosa and Sharpe agar), GYA (Glucose Yeast Extract Agar), TSB (Tryptone Soya Broth), Sporulation media and Mueller Hinton Agar.

In another related aspect, the isolated probiotic strain returns positive for biochemical tests catalase, oxidase, methyl red, voges proskauers, lactose, xylose, maltose, fructose, dextrose, galactose, raffinose, trehalose, melobiose, sucrose, arabinose, mannose, inulin, sodium gluconate, salicin, sorbitol, mannitol, arabitol, methyl glucoside, rhamnose, cellobiose, ONPG, esculin hydrolysis and negative for biochemical tests sorbose malonate utilization, citrate utilization, xylitol, methyl mannoside, melezitose, erythritol, adonitol, inositol, dulcitol, glycerol, blood hemolysis, citrate and indole.

In another preferred embodiment, the invention discloses a novel probiotic bacteria of the genus *Bacillus*, isolated from honey for increased utilization of fructose from foods rich in fructose. In another related aspect, the fructophilic probiotic bacterium is Gram positive. In yet another aspect, optimum pH and temperature recorded for the growth of fructophilic bacteria is 7.5 and 40° C. respectively. In another aspect, the fructophilic probiotic bacteria is bile tolerant, gastric acid resistance and produces lactic acid. In a related aspect, the fructophilic probiotic bacteria is *Bacillus coagulans*. In yet another related embodiment, the *Bacillus coagulans* strain is *Bacillus coagulans* MTCC 25235. In a related aspect, the foods rich in fructose are selected from the group comprising high fructose corn syrup, honey, Agave, Maple syrup, Coconut sugar, Palm sugar, Molasses, Soda, Candies, sweetened yogurt, frozen foods, canned foods, cereals, fruit juices, coffee creamer, jams and jellies, energy drinks, condiments, ice cream. In a related aspect, the fructophilic probiotic bacteria is used for the therapeutic management of disorders related to high fructose intake. In a related aspect, diseases related to high fructose intake are selected from the group comprising, but not limited, obesity, non-alcoholic steatohepatitis (NASH), insulin resistance, metabolic syndrome, cardio-vascular complications, diabetes, hyperlipidemia, hypertension, inflammation and hyperuricemia. In another related aspect, the fructophilic probiotic bacteria is present in the form of an inoculum, freeze-dried powder, fine powder, tablet, capsule, suspension, solution, emulsion, gummy, chewable or edible foods and administered as a stand-alone or in combination with foods rich in fructose selected from the group comprising high fructose corn syrup, honey, Agave, Maple syrup, Coconut sugar, Palm sugar, Molasses, Soda, Candies, sweetened yogurt, frozen foods, canned foods, cereals, fruit juices, coffee creamer, jams and jellies, energy drinks, condiments, ice cream.

In yet another preferred embodiment, the invention discloses a method of inhibiting pathogenic microbes said method comprising step of bringing to contact said microbes with the fructophilic probiotic bacteria *Bacillus coagulans* MTCC 25235. In a related aspect, the pathogenic microbes are selected from the group comprising *Salmonella abony, Micrococcus luteus, Escherichia coli, Pseudomonas aeruginosa, Bacillus cereus, Propionibacterium acnes, Streptococcus mutans, Staphylococcus aureus, Staphylococcus epidermidis*.

In another preferred embodiment, the invention discloses a method of producing short chain fatty acids by culturing the fructophilic probiotic bacteria *Bacillus coagulans* MTCC 25235 along with plant fibers selected from the group consisting of fructose, fenugreek seed fibers, cranberry seed fibers, fructooligosaccharides (FOS).

The specific examples included herein below illustrate the aforesaid most preferred embodiments of the present invention.

EXAMPLES

Example 1: Isolation and Identification of Fructophilic Bacteria

Methods

Raw unfiltered honey was used in this study to isolate the spore forming fructophilic lactic acid bacteria. For the isolation of fructophilic bacteria, de Man, Rogosa and Sharpe (MRS) (dextrose replaced by fructose) was used in this study (table 1).

TABLE 1

Media composition

| Sr. No. | Ingredients | Gms/Liter |
| --- | --- | --- |
| 1 | Proteose peptone | 10.000 |
| 2 | Beef extract | 10.000 |
| 3 | Yeast extract | 5.000 |
| 4 | Fructose | 20.000 |
| 5 | Polysorbate 80 | 1.000 |
| 6 | Ammonium citrate | 2.000 |
| 7 | Sodium acetate | 5.000 |
| 8 | Magnesium sulphate | 0.100 |
| 9 | Manganese sulphate | 0.050 |
| 10 | Dipotassium phosphate | 2.000 |
| 11 | Agar | 12.000 |
| 12 | Final pH (at 25° C.) | 6.5 ± 0.2 |

One gm of unfiltered raw honey was taken into the test tubes containing 10 ml of saline. This was mixed well and heat shock was given at 70° C. for 30 minutes for selective isolation of spores. Isolation of bacteria was carried out by adding 1 ml of above sample from each dilution onto the MRS agar plates containing fructose. Plates were further incubated at 37° C. for 48 h. After incubation, morphologically distinct colonies were picked up for further testing and purification of bacterial isolates. *Bacillus coagulans* MTCC 25235 was isolated and streaked on other MRS agar plate containing fructose as carbon source.

Biochemical Characterization of Fructophilic Bacteria

Bacterial isolates were grown in de Man, Rogosa and Sharpe Agar (MRSA) for 24 h at 37° C. Bacterial inoculums were prepared by picking 1 to 3 well isolated colonies and a homogenous suspension in sterile saline was prepared. The density of suspension was >0.5 OD at 620 nm. This inoculum (50 µl) of was used and test was performed as per the kit manufacturer's instructions (HiMedia, Mumbai, India). Biochemical characterization of *Bacillus coagulans* MTCC 25235 and *B. coagulans* ATCC 31284 was performed by the method described (Majeed, M., Nagabhushanam, K., Natarajan, S., Sivakumar, A., Eshuis-de Ruiter, T., Booij-Veurink, J., Janine Booij-Veurink, Ynte P. de Vries, Ali, F. (2016); Evaluation of genetic and phenotypic consistency of *Bacillus coagulans* MTCC 5856: A commercial probiotic strain. World Journal of Microbiology & Biotechnology, 32,60). HiCarbohydrate™ Kit (code-KB009) was procured from HiMedia, Mumbai, India and tests were performed as per the manufacturer's instructions. Bacterial suspension of *Bacillus coagulans* MTCC 25235 and *B. coagulans* ATCC 31284 was prepared as mentioned in above section. Further, IMViC (indole, methyl red, Voges Proskauer, Citrate utilization) test, oxidase and Gram staining of and *B. coagulans* ATCC 31280 were performed as per the method Majeed et al., (2016); (Cappucino G and Natalie Sherman. Microbiology: A Laboratory manual 5th edition. 1998).

16S rDNA Sequencing 16S rDNA sequencing Genomic DNA of the *B. coagulans* MTCC 5856 was prepared as previously described by (William J. Bruno, Nicholas D. Socci, and Aaron L. Halpern (2000). Weighted Neighbor Joining: A Likelihood-Based Approach to Distance-Based Phylogeny Reconstruction, Mol. Biol. Evol. 17 (1): 189-197). A fragment of the 16S rDNA gene was sequenced using an ABI 3500 genetic analyser automated DNA sequencer as described earlier (Heyrman and Swings 2001). The sequencing primers used were 5-AGHGTBTGHTCMTGNCTCAS-3 (Forward Primer) and 5-TRCGGYTMCCTTGTWHCGACTH-3 (Reverse Primer). The amplified DNA fragment of approximately 1.5 kb separated on a 1% agarose gel and purified by using Qiagen spin columns.

The purified fragment was used directly for DNA sequencing. This sequence was used in a BLAST search (blast.ncbi.nlm.nih.gov/Blast.cgi).

Growth Conditions of *Bacillus coagulans* MTCC 25235

The optimization of growth conditions for *Bacillus coagulans* MTCC 25235 was analyzed for different temperature and pH. MRSB media was prepared and adjusted pH to 4.5, 5.0, 5.5, 6.0, 6.5, 7.0, 7.5 and 8.0 with 2 N HCl and 2N NaOH. Overnight grown culture (1%, v/v) inoculated to pH adjusted media and incubated for 24 h in a shaking incubator at 120 rpm. Growth was monitored at every six hour interval of time by measuring absorbance at 600 nm using spectrophotometer (Shimadzu Corporation, Kyoto, Japan). MRSB media was prepared adjusted pH to 6.5 and inoculated with overnight grown culture (1%, v/v). Further, flasks were incubated for 24 h in shaking incubator at 120 rpm at different temperatures (20, 30, 37, 40, 50 and 60° C.). Growth was monitored at every six hour interval of time by measuring absorbance at 600 nm using spectrophotometer (Shimadzu Corporation, Kyoto, Japan).

Results

Identification of Fructophilic Bacteria

Figure 1A:
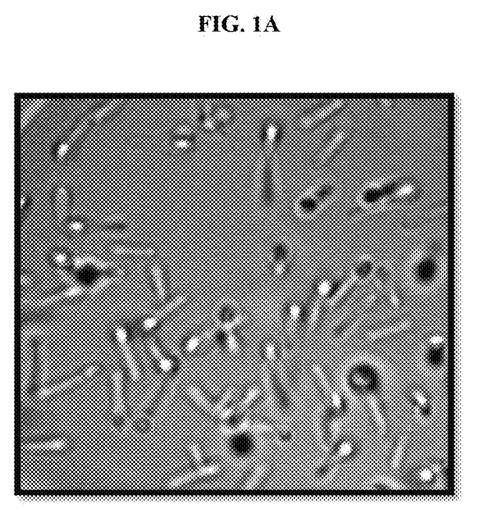
FIGS. 1A, 1B, 1C and 1D shows the phase contrast microscopic image (×1000 magnification) of *Bacillus coagulans* MTCC 25235 (FIG. 1A), wet mount of cells with the spores (FIG. 1B), Gram staining of vegetative cells (FIG. 1C), Spore staining of sporulated cells and (FIG. 1D), colony grown on GYE agar plate.
Figure 1B:
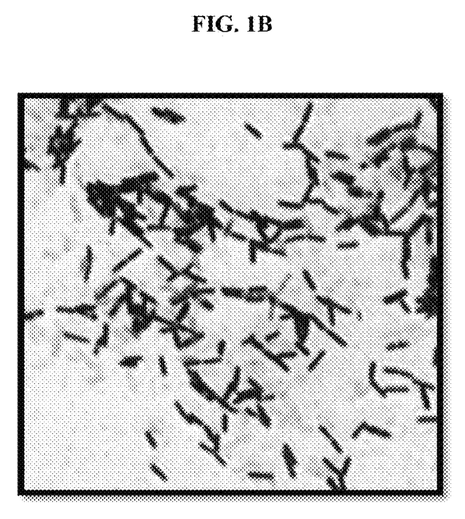
Figure 1C:
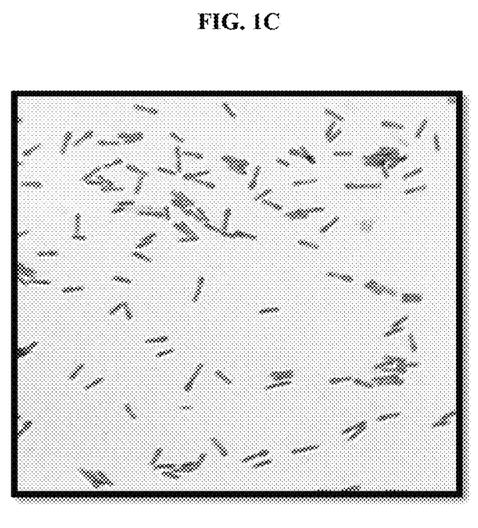
Figure 1D:
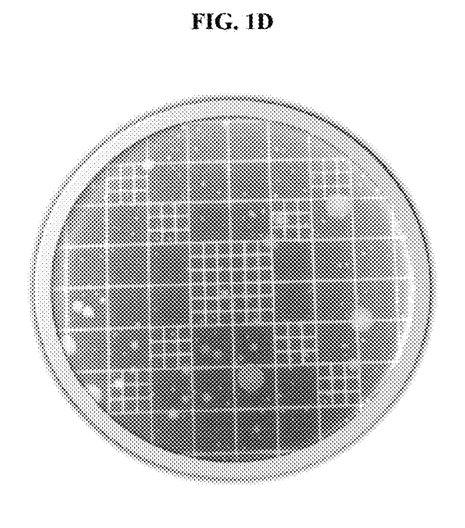
Figure 2:
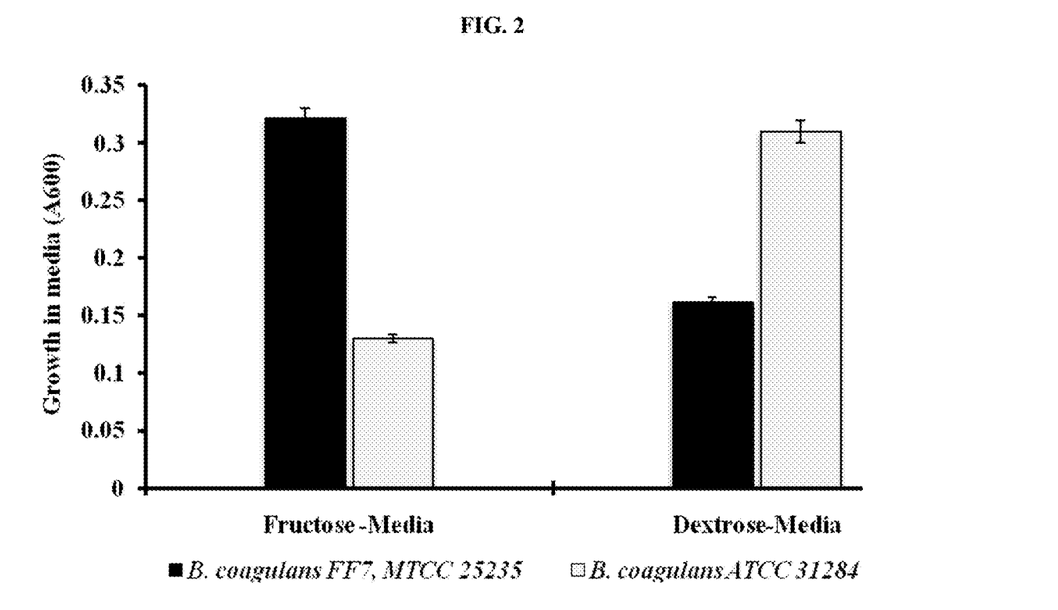
FIG. 2 shows graphical representation of comparison of growth pattern of *Bacillus coagulans* FF7, MTCC 25235 and *B. coagulans* ATCC 31284 in presence of fructose and dextrose as carbon source. Values are mean (±SD) from three independent determinations.
Figure 3:
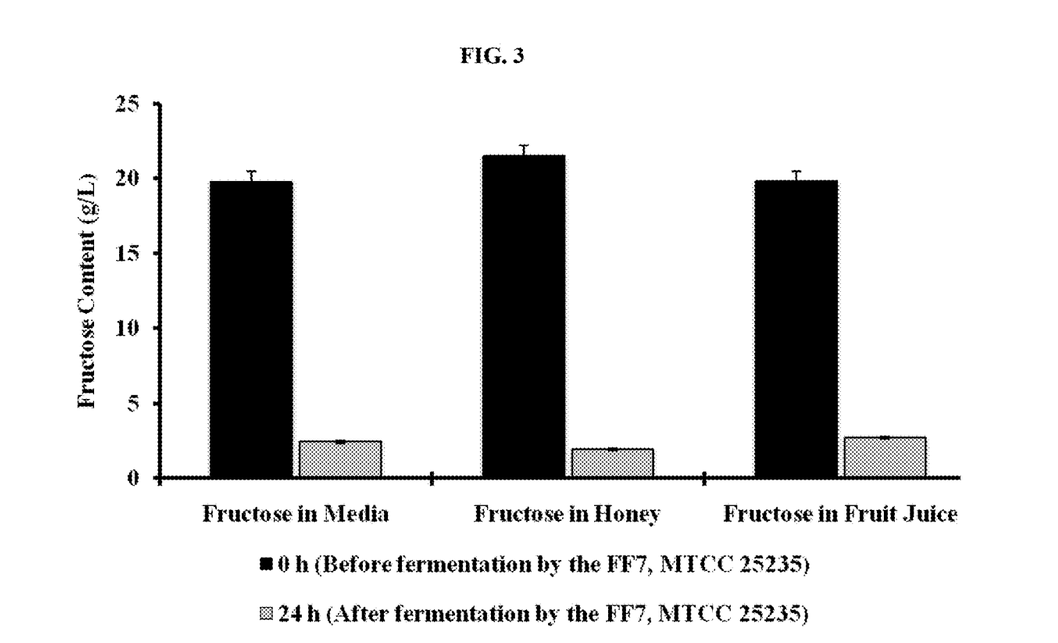
FIG. 3 shows graphical representation of utilization of fructose by *Bacillus coagulans* MTCC FF7, 25235 after 24 h of incubation in presence of media and fructose rich foods (Honey, fruit juice). Values are mean (±SD) from three independent determinations.

The spores of *Bacillus coagulans* MTCC 25235 were ellipsoidal terminal spores (FIG. 1A) and vegetative cells were Gram positive rod shaped as indicated in Gram's stain (FIG. 1B). Colonies from *B. coagulans* MTCC 25235 were grown on media, yielding uniform, 1-3 mm in diameter, white to cream, smooth colonies that contain vegetative rod shaped cells (FIGS. 1C and D). The growth of the isolated bacteria was better in fructose rich media rather than dextrose rich media (FIG. 2), indicating its fructophilic nature and fructose utilization potential when compared to other *Bacillus coagulans* strains. The growth of the bacterial was also tested in fructose rich food stuff and showed a deduction in the fructose content (FIG. 3) implying that the bacterium utilizes fructose as a carbon source for its growth and development. Thus, the bacterium can be used in managing and preventing disorders related to high fructose intake by utilizing the excess fructose in the food stuff for its metabolism. The bacteria can be administered as a stand alone or in combination with foods rich in fructose which include high fructose corn syrup, honey, Agave, Maple syrup, Coconut sugar, Palm sugar, Molasses, Soda, Candies, sweetened yogurt, frozen foods, canned foods, cereals, fruit juices, coffee creamer, jams and jellies, energy drinks, condiments, ice cream (Braverman J, List of Foods high in fructose, livestrong.com/article/30454-list-foods-high-fructose/, accessed 3 May 2019)

Biochemical Characterization

Biochemical characterization of *Bacillus coagulans* MTCC 25235 and *B. coagulans* ATCC 31284 was performed by the method described (Majeed, M., Nagabhushanam, K., Natarajan, S., Sivakumar, A., Eshuis-de Ruiter, T., Booij-Veurink, J., Janine Booij-Veurink, Ynte P. de Vries, Ali, F. (2016); Evaluation of genetic and phenotypic consistency of *Bacillus coagulans* MTCC 5856: A commercial probiotic strain. World Journal of Microbiology & Biotechnology, 32,60). The results were compared with commercial strain *B. coagulans* ATTCC 3128 and tabulated in Table 2.

TABLE 2

Biochemical characterization of *B. coagulans* ATTCC 3128 and *Bacillus coagulans* MTCC 25235

| S.No. | Tests | *B. coagulans* ATTCC 3128 | *B. coagulans* MTCC 25235 |
|---|---|---|---|
| 1. | Catalase | Positive | Positive |
| 2. | Oxidase | Positive | Positive |
| 3. | Indole | Negative | Negative |
| 4. | Methyl Red | Positive | Positive |
| 5. | Voges Proskauers | Positive | Positive |
| 6. | Citrate | Negative | Negative |
| 7. | Blood Hemolysis | Negative | Negative |
| 8. | Gram staining | Gram Positive | Gram Positive |
| 9. | Lactose | Positive | Positive |
| 10. | Xylose | Positive | Positive |
| 11. | Maltose | Positive | Positive |
| 12. | Fructose | Positive | Positive |
| 13. | Dextrose | Positive | Positive |
| 14. | Galactose | Positive | Positive |
| 15. | Raffinose | Positive | Positive |
| 16. | Trehalose | Positive | Positive |
| 17. | Melobiose | Positive | Positive |
| 18. | Sucrose | Positive | Positive |
| 19. | L-Arabinose | Positive | Positive |
| 20. | Mannose | Positive | Positive |
| 21. | Inulin | Positive | Positive |
| 22. | Sodium gluconate | Positive | Positive |
| 23. | Glycerol | Negative | Negative |
| 24. | Salicin | Positive | Positive |
| 25. | Dulcitol | Negative | Negative |
| 26. | Inositol | Negative | Negative |
| 27. | Sorbitol | Positive | Positive |
| 28. | Mannitol | Positive | Positive |
| 29. | Adonitol | Positive | Negative |
| 30. | Arabitol | Positive | Positive |
| 31. | Erythritol | Negative | Negative |
| 32. | α-Methyl-D-glucoside | Positive | Positive |
| 33. | Rhamnose | Positive | Positive |
| 34. | Cellobiose | Positive | Positive |
| 35. | Melezitose | Negative | Negative |
| 36. | α-Methyl-D-mannoside | Negative | Negative |
| 37. | Xylitol | Negative | Negative |
| 38. | ONPG | Positive | Positive |
| 39. | Esculin hydrolysis | Positive | Positive |
| 40. | D-Arabinose | Positive | Positive |
| 41. | Citrate utilization | Negative | Negative |
| 42. | Malonate utilization | Negative | Negative |
| 43. | Sorbose | Negative | Negative |

The results indicated that the isolated probiotic strain is positive for biochemical tests catalase, oxidase, methyl red, voges proskauers, lactose, xylose, maltose, fructose, dextrose, galactose, raffinose, trehalose, melobiose, sucrose, melobiose, arabinose, mannose, inulin, sodium gluconate, salicin, sorbitol, mannitol, arabitol, methyl glucoside, rhamnose, cellobiose, ONPG, esculin hydrolysis and negative for biochemical tests sorbose malonate utilization, citrate utilization, xylitol, methyl mannoside, melezitose, erythritol, adonitol, inositol, dulcitol, glycerol, blood hemolysis, citrate and indole.

16S rDNA Sequencing

The bacterial 16S rDNA was sequenced and the sequence information (SEQ ID) was obtained as below:

```
LOCUS seq_FF7 1437 bp
ORIGIN
    1 ACTTGCAAGT CGTGCGGCCC TTTTTTAAAA
      GCTTGCTTTT TAAAAGGTTA GCGGCGGACG
   61 GGTGAGTAAC ACGTGGGCAC CCTGCCTGTA
      AGATCGGGAT AACGCCGGGA AACCGGGGCT
  121 AATACCGGAT AGTTTTTTCC TCCGCATGGA
      GGAAAAAGGA AAGACGGCTT CTGCTGTCAC
  181 TTACAGATGG GCCCGCGGCC CATTAGCTAG
      TTGGTGGGGT AACGGCTCAC CAAGGCAACG
  241 ATGCGTAGCC GACCTGAGAG GGTGATCGGC
      CACATTGGGA CTGAGACACG GCCCAAACTC
  301 CTACGGGAGG CAGCAGTAGG GAATCTTCCG
      CAATGGACGA AAGTCTGACG GAGCAACGCC
  361 GCGTGAGTGA AGAAGGCCTT CGGGTCGTAA
      AACTCTGTTG CCGGGGAAGA ACAAGTGCCG
  421 TTCGAACAGG GCGGCGCCTT GACGGTACCC
      GGCCAGAAAG CCACGGCTAA CTACGTGCCA
  481 GCAGCCGCGG TAATACGTAG GTGGCAAGCG
      TTGTCCGGAA TTATTGGGCG TAAAGCGCGC
  541 GCAGGCGGCT TCTTAAGTCT GATGTGAAAT
      CTTTGCGGGC TCACCCGCAA GCGGTCATTG
  601 GAAACTGGGA GGGCTTTGAG TGCAAGAAAG
      AGGAGAGTGG AATTTCCACG TGTAGCGGTG
  661 AAATGCGTAA AGATGTGGAG GAACACCAGT
      GGCGAAGGCG GCTCTCTGGT CTGTAACTGA
  721 CGCTGAGGCG CGAAAGCGTG GGGAGCAAAC
      AGGATTAGAT ACCCTGGTAG TCCACGCCGT
  781 AAACGATGAG TGCTAAGTGT TAGAGGGTTT
      CCGCCCTTTA GTGCTGCAGC TAACGCATTA
  841 AGCACTCCGC CTGGGGAGTA CGGCCGCAAG
      GCTGAAACTC AAAGGAATTG ACGGGGGCCC
  901 GCACAAGCGG TGGAGCATGT GGTTTAATTC
      GAAGCAACGC GAAGAACCTT ACCAGGTCTT
  961 GACATCCTCT GACCTCCCTG AGACAGGGC
      CTTCCCCTTC GGGGGACAGA GTGACAGGTG
 1021 GTGCATGGTT GTCGTCAGCT CGTGTCGTGA
      GATGTTGGGT TAAGTCCCGC AACGAGCGCA
 1081 ACCCTTGACC TTAGTTGCCA GCATTCAGTT
      GGGCACTCTA AGGTGACTGC CGGTGACAAA
 1141 CCGGAGGAAG GTGGGGATGA CGTCAAATCA
      TCATGCCCCT TATGACCTGG GCTACACACG
 1201 TGCTACAATG GATGGTACAA AGGGCTGCGA
      GACCGCGAGG TTAAGCCAAT CCCAGAAAAC
 1261 CATTCCCAGT TCGGATTGCA GGCTGCAACC
      CGCCTGCATG AAGCCGGAAT CGCTAGTAAT
 1321 CGCGGATCAG CATGCCGCGG TGAATACGTT
      CCCGGGCCTT GTACACACCG CCCGTCACAC
 1381 CACGAGAGTT TGTAACACCC GAAGTCGGTG
      AGGTAACCTT ACGGAGCCAG CCGCCGA
//
```

A BLAST (Basic local alignment search tool) search was performed with the above sequence and results of the first 10 alignment sequences are tabulated in table 3.

TABLE 3

Alignment view using combination of NCBI GenBank - Distribution of 10 Blast Hits on the Query Sequence

| S. No. | Description | Max score | Total score | Query cover | E value | Ident | Accession |
|---|---|---|---|---|---|---|---|
| 1 | *Bacillus coagulans* strain 55-LR4 16S ribosomal RNA gene, partial sequence | 2562 | 2562 | 100% | 0.0 | 98.96% | MF077122.1 |
| 2 | *Bacillus coagulans* strain KCCM203098 16S ribosomal RNA gene, partial sequence | 2556 | 2556 | 100% | 0.0 | 98.89% | MF992239.1 |
| 3 | *Bacillus* sp. MC-02 gene for 16S ribosomal RNA, partial sequence | 2556 | 2556 | 99% | 0.0 | 98.95% | AB849115.1 |

TABLE 3-continued

Alignment view using combination of NCBI GenBank -
Distribution of 10 Blast Hits on the Query Sequence

| S. No. | Description | Max score | Total score | Query cover | E value | Ident | Accession |
|---|---|---|---|---|---|---|---|
| 4 | *Bacillus coagulans* gene for 16S ribosomal RNA, partial sequence, strain: NTUIOB YUN2 | 2556 | 2556 | 100% | 0.0 | 98.89% | AB696800.1 |
| 5 | *Bacillus coagulans* gene for 16S rRNA, strain: T5 | 2556 | 2556 | 100% | 0.0 | 98.89% | AB240205.1 |
| 6 | *Bacillus coagulans* strain ICMP 22322 16S ribosomal RNA gene, partial sequence | 2553 | 2553 | 100% | 0.0 | 98.82% | MH392659.1 |
| 7 | *Bacillus* sp. IMM05 partial 16S rRNA gene, strain IMM05 | 2553 | 2553 | 100% | 0.0 | 98.82% | FR727705.1 |
| 8 | Uncultured *Bacillus* sp. clone Bco 16S ribosomal RNA gene, partial sequence | 2551 | 2551 | 100% | 0.0 | 98.82% | MG557779.1 |
| 9 | *Bacillus coagulans* DSM 1 = ATCC 7050, complete genome | 2529 | 2529 | 100% | 0.0 | 98.54% | CP009709.1 |
| 10 | *Bacillus coagulans* strain ATCC 7050 16S ribosomal RNA gene, partial sequence | 2505 | 2505 | 100% | 0.0 | 98.19% | NR_115727.1 |

Figure 4:
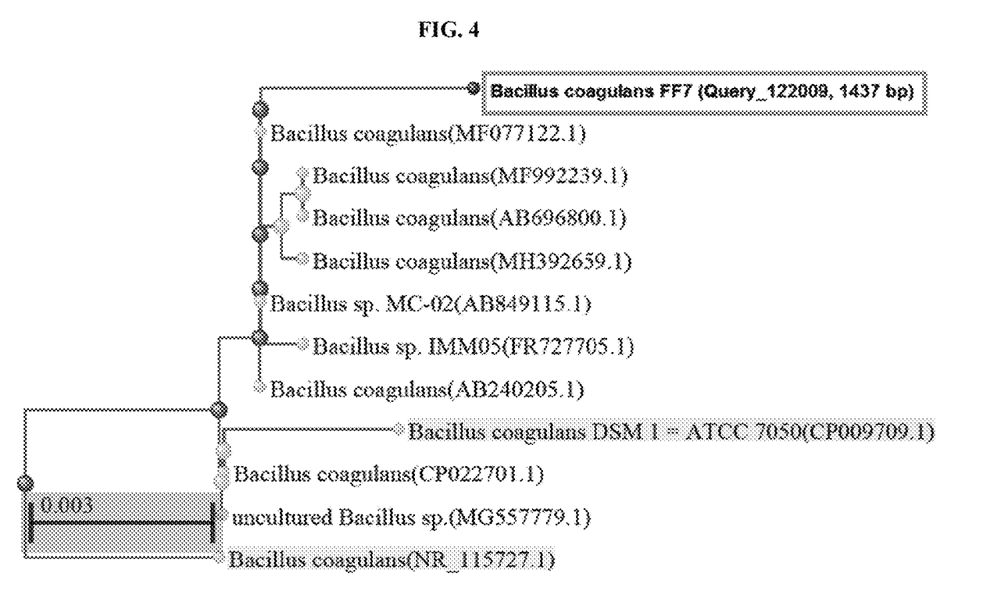
FIG. 4 shows phylogenetic tree based on the sequence of 16S rRNA showing the relative positions of *Bacillus coagulans* FF7.

The results indicated that the isolated organism is a new strain of *Bacillus coagulans* having 98.96% identity with *Bacillus coagulans* strain 55-LR4. The results of the phylogenetic analysis also indicated that the organism is a new strain of *Bacillus coagulans* (FIG. 4)

Optimum of the Growth Conditions for Fructophilic Bacteria

Figure 5:
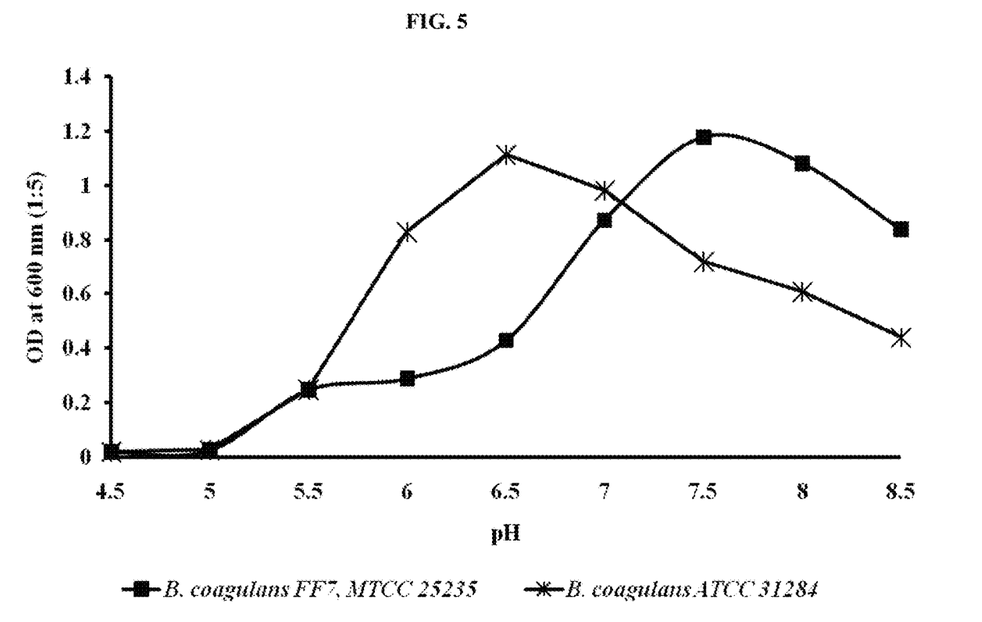
FIG. 5 shows effect of different pH on the growth of *B. coagulans* FF7, MTCC 25235 and *B. coagulans* ATCC 31284, optimum pH for the growth was found to be pH 7.5 and pH 6.5 respectively. Values are mean (±SD) from three independent determinations.
Figure 6:
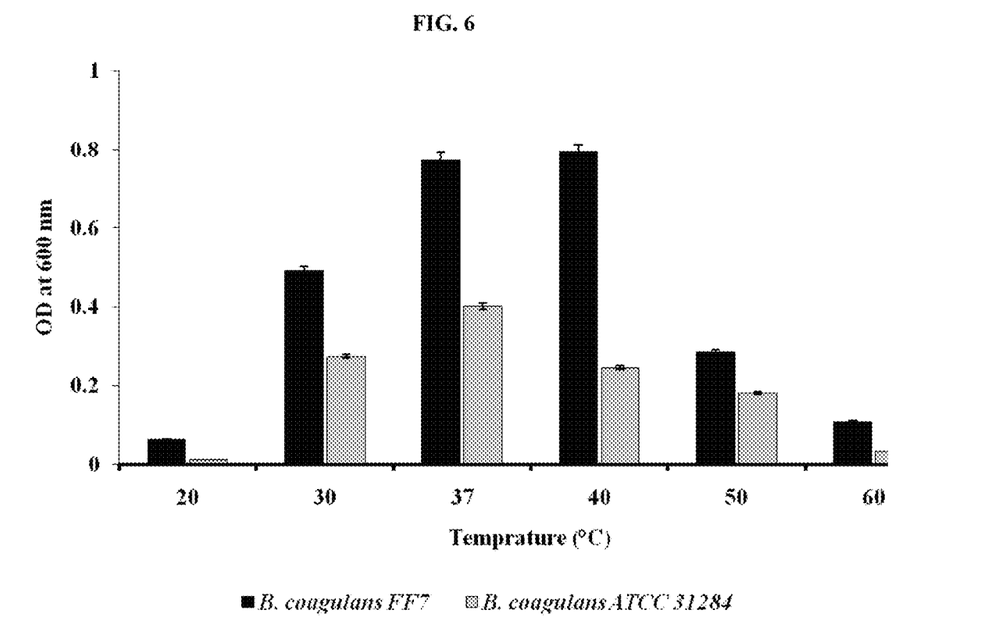
FIG. 6 shows graphical representation of effects of different temperatures on the growth of *B. coagulans* MTCC FF7, 25235 and *B. coagulans* ATCC 31284. Values are mean (±SD) from three independent determinations.

The optimum pH and temperature recorded for the growth of fructophilic bacteria was 7.5 and 40° C. respectively (FIG. 5 and FIG. 6)

Example 2: In Vitro Probiotic Evaluation of *Bacillus coagulans* MTCC 25235

Resistance to Gastric Acid

The survival of *Bacillus coagulans* MTCC 25235 spores was studied by addition of 1 ml of suspension into 100 ml of a sterile electrolyte solution (6.2 g/L NaCl, 2.2 g/L KCl, 0.22 g/L $CaCl_2$), and 1.2 g/L $NaHCO_3$) containing 0.01% lysozyme (Sigma-Aldrich) and 0.3% pepsin (Sigma-Aldrich) and incubated for 5 min. Further, pH was adjusted to 1.5, 3, 4, 5, 6, 7 and 8 (adjusted using 1 N NaOH and 1 N HCl). Incubation temperature was monitored to 37° C. for 4 h. One ml of sample was withdrawn at different time intervals at 0, 1.0, 2.0, 3.0 and 4.0 h. After incubation, serial dilution was done in sterile saline (0.89% w/v) and the viable count was enumerated by plating on glucose yeast extract agar (HiMedia). Experiments were performed in triplicate at two different occasions.

Bile Salt Tolerance

Bile tolerance of *Bacillus coagulans* MTCC 25235 cells was determined by the method described earlier (Gilliland et al. 1984; Hyronimus et al. 2000). MRS broth (HiMedia) was inoculated with approximately $10^6$ cfu $mL^{-1}$ of *Bacillus coagulans* MTCC 25235 overnight grown culture and then supplemented with (0.1, 0.2, 0.3, 0.4, 0.5, 0.6, 0.7, 0.8, 0.9, 1.0, 1.5 and 2.0%, w/v) bile salt and without bile salt as control in the experiment. Samples were incubated for 24 h at 37° C. with shaking at 120 rpm. Growth in control (no bile) and test cultures at different concentrations of bile was monitored hourly by measuring absorbance at 600 nm using spectrophotometer (Shimadzu Corporation, Kyoto, Japan).

Production of Lactic Acid

Lactic acid production by *Bacillus coagulans* MTCC 25235 was estimated by using a Megazyme kit. A loopful of an overnight grown culture of *Bacillus coagulans* MTCC 25235 was added to glucose yeast extract broth (HiMedia) and incubated at 37° C. for 18 h with 120 rpm. After incubation, the broth was filtered through 0.22 micron (Sartorius, India) and analyzed for lactic acid content by using Megazyme kit (K-DLATE 10/04) as per instructions (Megazyme International Ireland, IDA Business Park, Wicklow, Ireland). GYE media was taken as blank in the assay.

Simulated Gastric Juice Tolerance

Figure 7:
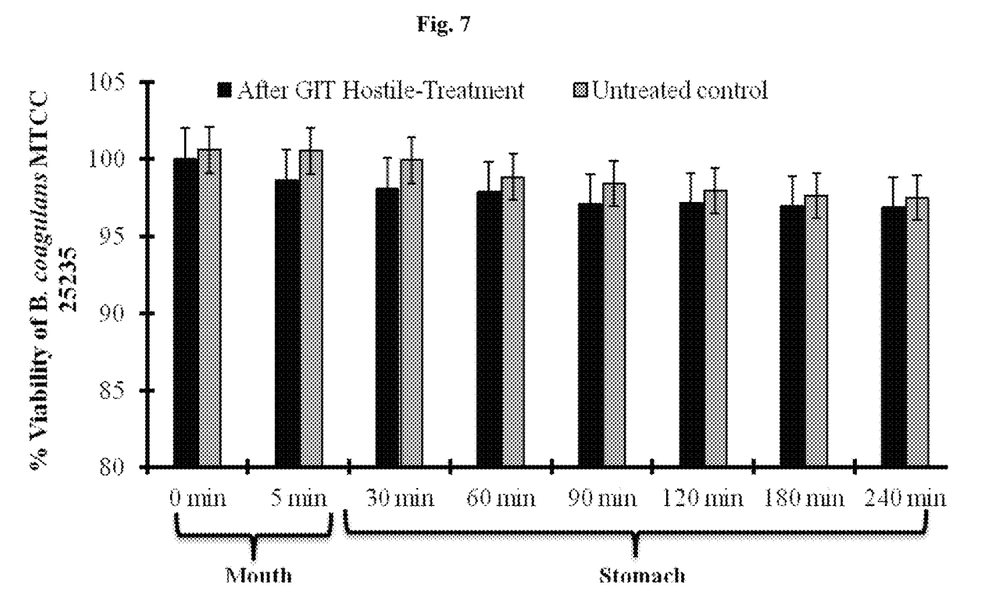
FIG. 7 shows Effect of GIT hostile conditions on the viability of *B. coagulans* MTCC 25235 after gastric treatment in an in-vitro experiment mimicking invivo conditions. Sterile saline was taken as untreated control.

The survival of *Bacillus coagulans* MTCC 25235 spores was studied to represent buccal digestion conditions. One mL of the suspension of *Bacillus coagulans* MTCC 25235 was subjected to stimulated salivary juice contents consist of KCl (0.8946 g/l), $CO(NH_2)_2$ (0.1981 g/L), $Na_2SO_4$ (0.5681 g/L), NaHCO; (1.680 g/L), $NaH_2PO_4$ (0.8878 g/L), pH adjusted to 6.8±0.2 and incubated at 37° C. for 5 min. Further, simulated gastric juice was prepared by adding 9 g/L of sodium chloride and 3 g/L of pepsin (Sigma-Aldrich, St. Louis, MO, USA) and then the pH was adjusted to aseptically 3.0±0.2 by using 2 N HCl. Samples were further incubated at 37° C. for 3 h with low r.p.m. After 3 h of incubation, pH was adjusted aseptically to 7.0 using 2 N NaOH. Ox bile (5 g/L) this was further incubated at 37° C. for 24 h. After final step of the simulated digestion process, samples were collected and evaluated for the spore survival of *Bacillus coagulans* MTCC 25235 was enumerated by serial dilution method using glucose yeast extract agar media (HiMedia) (FIG. 7).

Antibiotic Resistance Pattern

MIC was determined as per the guidelines of Clinical and Laboratory Standards Institute (CLSI 2012). *Bacillus coagu-*

*lans* MTCC 25235 suspensions were prepared by suspending 18 h grown bacterial culture in sterile normal saline (0.89% NaCl wt/vol; Himedia, Mumbai India). The turbidity of the bacterial suspension was adjusted to 0.5 McFarland standards (equivalent to $1.5 \times 10^8$ colony forming units (CFU)/ml). The antibiotics stock solutions were prepared as per CLSI guidelines and 2-fold serial dilutions were prepared in broth medium (glucose yeast extract acetate broth [GYEA, HiMedia, Mumbai India for *Bacillus coagulans* MTCC 25235 and Mueller Hinton Broth [MHB, Difco Laboratories, Detroit, Mich USA] for *S. aureus*) in 100 µl volume in 96-well U bottom microtiter plates (BD Labware, NJ USA). The above-mentioned bacterial suspension was further diluted in the MHB and 100 µl volume of this diluted inoculum was added to each well of the plate resulting in the final inoculum of $5 \times 10^5$ CFU/ml in the well and the final concentration of antibiotics ranged from 0.0078 to 4 µg/ml. *S. aureus* ATCC 6538 was used as reference culture in this study. The plates were incubated at 37° C. for 24 h and were visually read for the absence or presence of turbidity. The minimum concentration of the compound concentration showing no turbidity was recorded as MIC.

Ames Test

The data of the experiment suggested that the *B. coagulans* MTCC 25235 spores did not increase the number of revertants in five *Salmonella* strains (TA98, TA100, TA102, TA1535 and TA1537), compared with their negative controls, either absence or presence of the S9 metabolic activation system. Further, no dose-dependent mutagenic effects were caused by the *B. coagulans* MTCC 25235 spores (up to 5000 µg/plate). *B. coagulans* MTC 25235 spores did not show any mutagenic activity under the experimental conditions.

BSH Activity

Figure 8A:
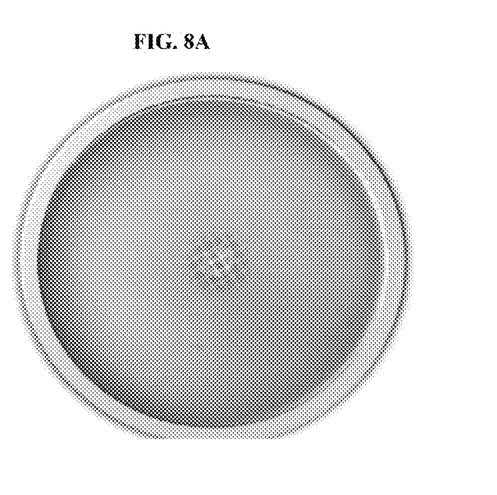
FIG. 8A shows the zone of inhibition (hollow zones) in petridish treated with *Bacillus coagulans* MTCC 25235.
Figure 8B:
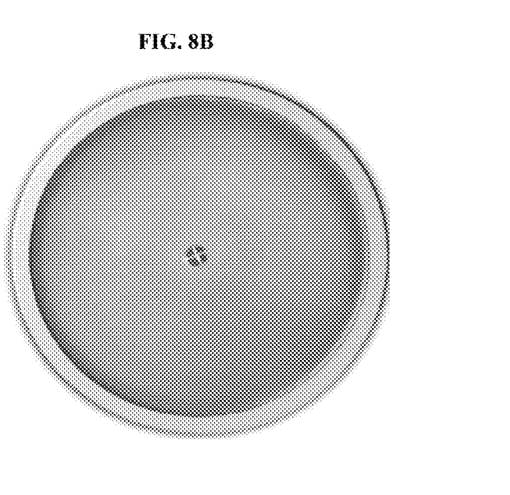
FIG. 8B is a negative control wherein the activity is determined using soft MRS agar supplemented with ox bile (0.3%, w/v) and CaCO3 (0.3%, w/v) and MRS agar without bile salts.

*Bacillus coagulans* MTCC 25235 growth was observed on an agar plate containing ox bile and calcium carbonate, which indicates its tolerance against ox bile and the presence of BSH activity. There was 19±2 mm clear zone in the soft agar plate as shown in (FIGS. 8A and 8B) which indicated the presence of BSH activity.

Antimicrobial Activity Against Human Pathogens

The antimicrobial activity was performed by a well diffusion assay as previously described with minor modifications (Cintas L M, Rodriguez J M, Fernandez M F, Sletten K, Nes I F, Hernandez P E, Holo H (1995) Isolation and characterization of pediocin L50, a new bacteriocin from *Pediococcus acidilactici* with a broad inhibitory spectrum. Appl Environ Microbiol 61:2643-2648). Briefly, a 5 mL lawn of soft (0.7% agar) glucose yeast extract (HiMedia, India), containing $10^6$ cfu mL$^{-1}$) of the indicator strains (*S. epidermidis* ATCC 14990, *S. mutans* MTCC 1943, *S. aureus* ATCC 29213, *B. cereus* ATCC 14579, *P. acnes* ATCC 11827, *E. coli* ATCC 25922, *P. aeruginosa* ATCC 9027, *M. luteus* NCIM 216 and *S. abony* NCIM 2257) was poured on top of an enriched hard (1.5% agar) tryptic soya agar (HiMedia, India). A loopful of overnight grown culture *B. coagulans* MTCC 25325 was added to MRS media and incubated for 24 h at 37° C. with 120 rpm. After 24 h, the culture was centrifuged (10,000×9 g) to remove the cells and the supernatant was collected, concentrated tenfold by lyophilization and filter-sterilized through a 0.22 micron filter (Sartorius, India). Concentrated supernatant (50 µL) was added to 6-mm wells punched in the solidified bi-layer agar. Plates were kept in the refrigerator (4±2° C.) for 5 h to allow the sample to diffuse into the agar and subsequently incubated at 37° C. for 18-20 h. After incubation, the zone of inhibition was measured and recorded in mm.

Production of Short Chain Fatty Acids

The in vitro fermentation with the *Bacillus coagulans* MTCC 25235 was carried out by following method described by McBurney and Thompson (1987) with some modifications. Briefly, 2.0 g of fructose, fenugreek seeds, cranberry seed fiber, FOS, were added to 100 ml of demineralised water. The pH was adjusted to 7.0±0.2 and autoclaved at 121° C. for 20 min. After sterilization, oxygen reducing enzyme Oxyrase (Oxyrase® for Broth, Oxyrase, Inc, OH, USA) was added to each flask, to induce anaerobic conditions. Five percent of overnight grown *Bacillus coagulans* MTCC 25235 culture was inoculated to all the flasks and incubated at 37° C. with gentle shaken rpm for 24 h. The bottles were tightly closed and sealed with parafilm to maintain anaerobic conditions generated by the enzyme supplement. The pH values at 0 h of incubation and after fermentation (24 h) were also recorded. One ml of copper sulphate (10 g/L) was added to each sample to inhibit further microbial growth (Sigma-Aldrich, St. Louis, MO, USA). Further, 5.0 ml of samples were added to 5 ml of distilled water and pH was adjusted to 1.5 using 3 M $H_2SO_4$. 10 ml of chilled diethyl ether (−20° C.) was added to samples and then vortex for 1 minute. Sodium chloride was added and then centrifuged at 3000×g for 10 minutes. After centrifugation, organic layer was separated and transferred to the fresh vial. This was used to quantify SCFAs. The SCFA standards were purchased from Sigma-Aldrich (St. Louis, MO, USA) and similarly processed. SCFA production (acetate, propionate and butyrate) was measured by gas chromatography (GC) with the use of a Agilent technologies 6890N gas chromatograph (Stevens Creek Blvd Santa Clara, CA, USA) containing a DB-FFAP (Terephthalic acid modified poly ethylene Glycol) column. The column temperature was 200° C. The injector and detector port temperatures were 250° C. The carrier gas was $N_2$ at a flow rate of 1.0 ml/min. SCFA standards were purchased from Sigma-Aldrich (St. Louis, Mo., USA). SCFA (Acetate, propionate and butyrate) concentrations were expressed in mg/gram of galactomannan from fenugreek seeds.

Result

Resistance to Gastric Acid

Figure 9:
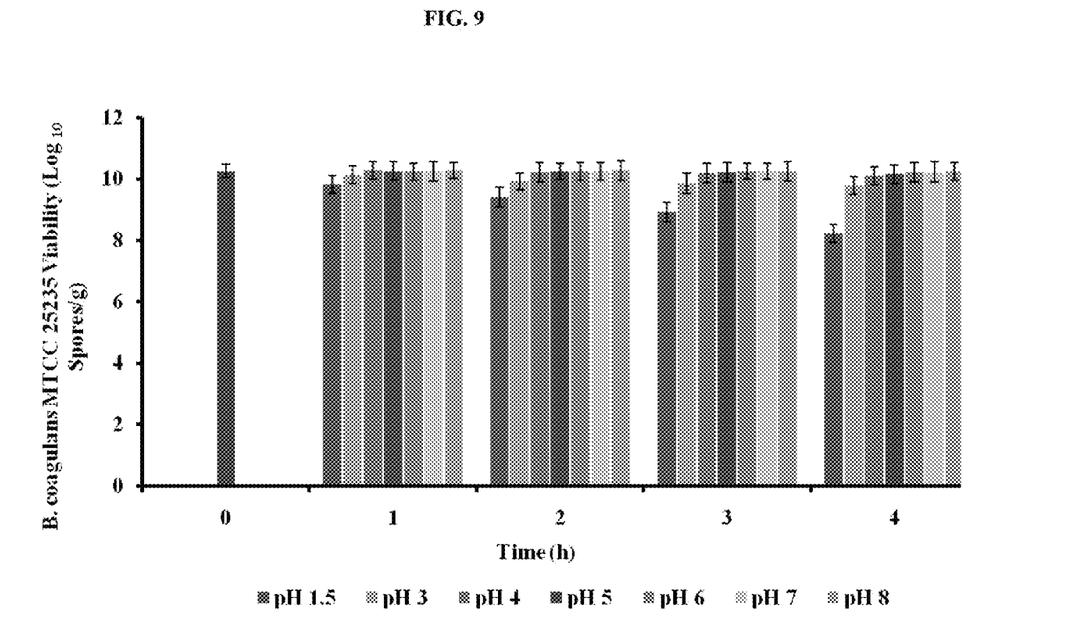
FIG. 9 shows graphical representation of the survival of *Bacillus coagulans* MTCC FF7, 25235 at various pH values (1.5-8.0) in gastric juice buffer. The values are expressed in Log 10 spores/g. Data represent the mean and standard deviations (±SD) of two different experiments performed.

There was no significant difference (2-5%) in spore count at pH 3 to pH 8.0 in comparison to the initial spore count up to 4 h of the study (FIG. 9). However, 0.44 and 2.036 $\log_{10}$ reduction was observed at pH 1.5 in 1 and 4 h respectively. Results of the study confirmed the stability of *Bacillus coagulans* MTCC 25235 spores in acidic as well as alkaline pH conditions.

Bile Tolerance Test

Figure 10:
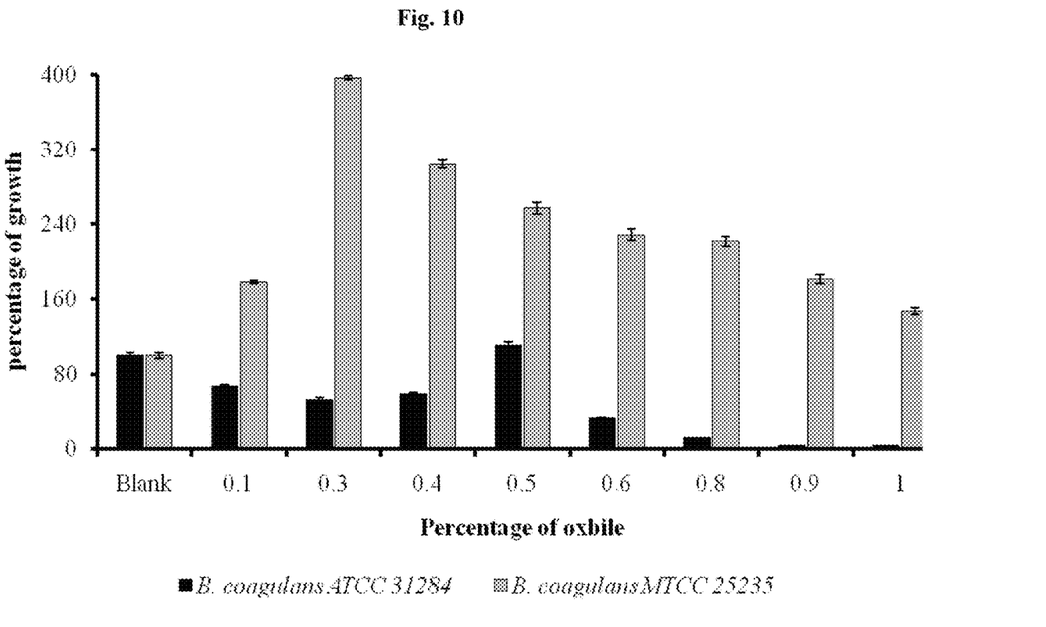
FIG. 10 shows graphical representation of in-vitro effect of ox bile salt on the growth of *B. coagulans* FF7, MTCC 25235 and *B. coagulans* ATCC 31284. The overnight grown fresh culture of *B. coagulans* MTCC 25235 and *B. coagulans* ATCC 31284 were inoculated in MRS broth with (0.1, 0.3, 0.4, 0.5, 0.6, 0.8, 0.9 and 1%, w/v) and without ox bile salt (%, w/v). Values are mean (±SD) from three independent determinations.

*Bacillus coagulans* MTCC 25235 growth was observed on the agar plate containing bile salt (1% w/v) which indicated its tolerance against bile salt. Further, bile tolerance assay was performed by supplementing (0.1-2.0%) ox bile to the MRS broth in different flask. *Bacillus coagulans* MTCC 25235 growth observed in presence and absence of ox bile up to 2%, w/v. Whereas, growth of *B. coagulans* ATCC 31284 was found in 0.8% w/v (FIG. 10). Similarly, there was no significant difference in the viability of *Bacillus coagulans* MTCC 25235 and *B. coagulans* ATCC 31284 in the presence and absence of bile salt.

Production of Lactic Acid

Figure 11:
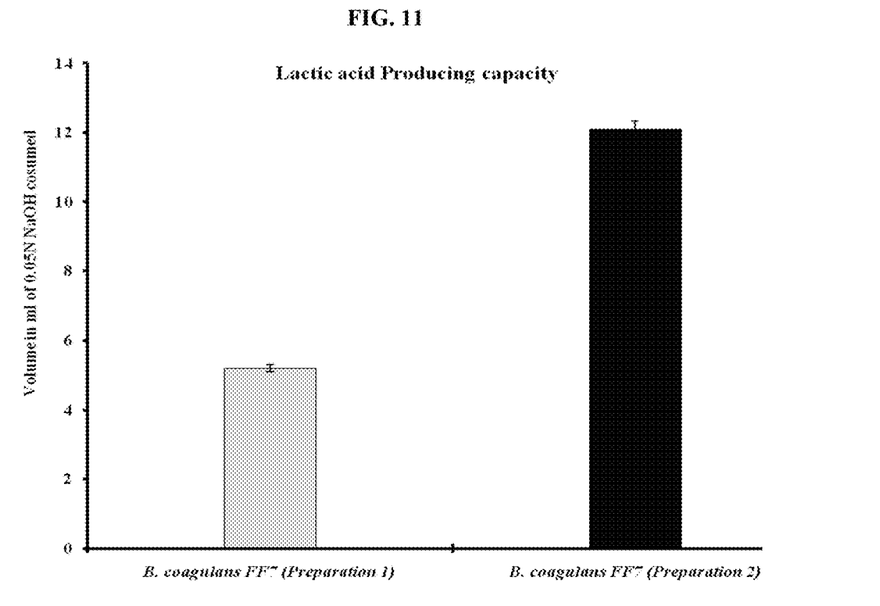
FIG. 11 shows graphical presentation of production of L-Lactic acid by *B. coagulans* FF7, MTCC 25235 in presence of two standardized preparations equivalent to $6 \times 10^9$ (preparation 1) and $15 \times 10^9$ cfu/g (preparation 2) were studied. Values are mean (±SD) from three independent determinations.

Lactic acid production by *Bacillus coagulans* MTCC 25235 was estimated by using a Megazyme kit. The total lactic acid produced by *Bacillus coagulans* MTCC 25235 was 4.487 g/L. L-form of lactic acid was 4.12 g/L. Whereas, D-form of lactic acid *Bacillus coagulans* MTCC 25235 is 0.367 g/L. (FIG. 11)

Antibiotic Resistance

MIC results of clindamycin, kanamycin, ampicillin, streptomycin, vancomycin, erythromycin, gentamicin, tetracycline and chloramphenicol against the *Bacillus coagulans* MTCC 25235 and *S. aureus* ATCC 6538 is given in table 4. All the antibiotics tested showed a MIC range of 0.0078 to 1.0 µg/ml against *Bacillus coagulans* MTCC 25235. All tested antibiotics exhibited a MIC range of 0.031 to 2 µg/ml against *S. aureus* ATCC 6538.

TABLE 4

Minimum inhibitory concentrations of antibiotics against *Bacillus coagulans* MTCC 25235 cultures and *S. aureus* ATCC 6538

| | | MIC (µg/ml)* | |
|---|---|---|---|
| S.No. | Antibiotics | *Bacillus coagulans* MTCC 25235 | *S. aureus* ATCC 6538 |
| 1 | Clindamycin hydrochloride | 0.25 | 0.062 |
| 2 | Kanamycin sulphate | 0.062 | 7.0 |
| 3 | Ampicillin sodium salt | 0.125 | 0.031 |
| 4 | Streptomycin sulphate | 0.062 | 4.0 |
| 5 | Vancomycin hydrochloride | 0.25 | 0.5 |
| 6 | Erythromycin | 0.125 | 0.125 |
| 7 | Gentamicin sulphate | 0.06 | 0.25 |
| 8 | Tetracycline hydrochloride | 0.03 | 0.062 |
| 9 | Chloramphenicol | 0.031 | 2.0 |

Antimicrobial Activity

The antimicrobial activity of *B. coagulans* MTCC 25235 was evaluated. Anti-microbial activity was determined by well diffusion assay as described by Cintas et al. (1995). The results indicated that the probiotic bacteria is an effective antimicrobial agent against *Salmonella abony, Micrococcus luteus, Escherichia coli, Pseudomonas aeruginosa, Bacillus cereus, Propionibacterium acnes, Streptococcus mutans, Staphylococcus aureus, Staphylococcus epidermidis*.

TABLE 4

Antimicrobial activity of *B. coagulans* MTCC 25235 against tested bacteria

| S. no. | Tested organism | Zone of inhibition |
|---|---|---|
| 1 | *Salmonella abony* NCIM 2257 | 14.00 ± 1.0 |
| 2 | *Micrococcus lutens* NCIM 2169 | 18.50 ± 1.6 |
| 3 | *Escherichia coli* ATCC 25922 | 19.00 ± 2.0 |
| 4 | *Pseudomonas aeruginosa* ATCC 9027 | 17.42 ± 1.8 |
| 5 | *Bacillus cereus* ATCC 14579 | 17.00 ± 2.1 |
| 6 | *Propionibacterium acnes* ATCC 11827 | 16.50 ± 1.2 |
| 7 | *Streptococcus mutans* MTCC 1943 | 17.50 ± 1.75 |
| 8 | *Staphylococcus aureus* ATCC 29213 | 15.85 ± 1.25 |
| 9 | *Staphylococcus epidermidis* ATCC 14990 | 14.85 ± 1.40 |

Figure 12A:
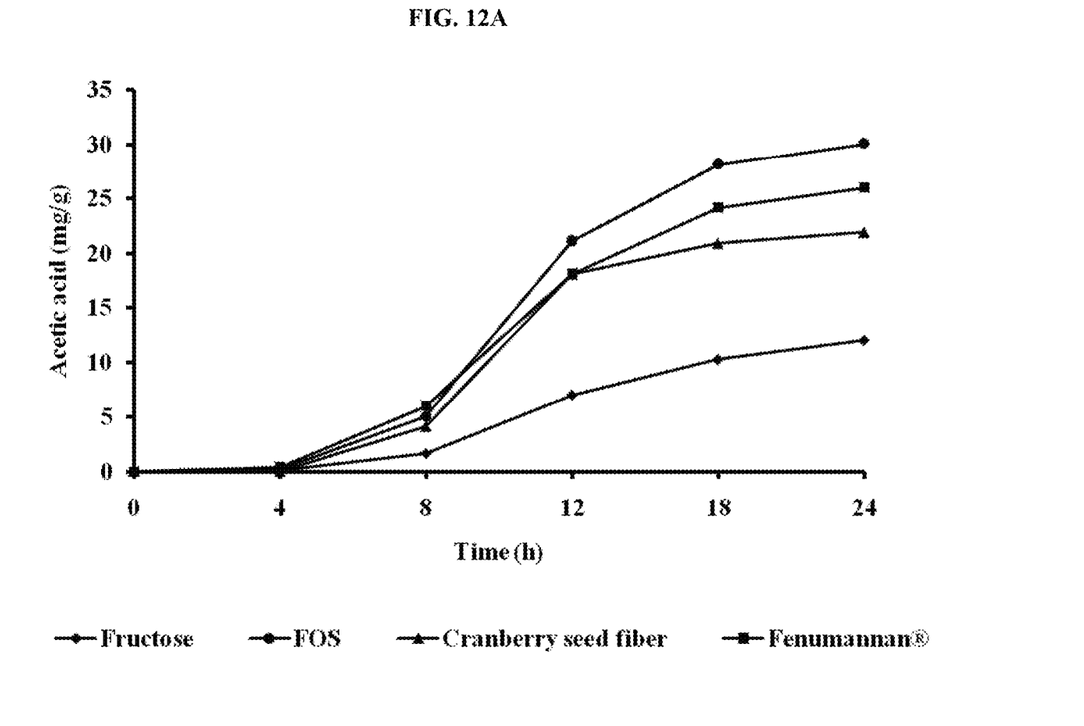
Figure 12B:
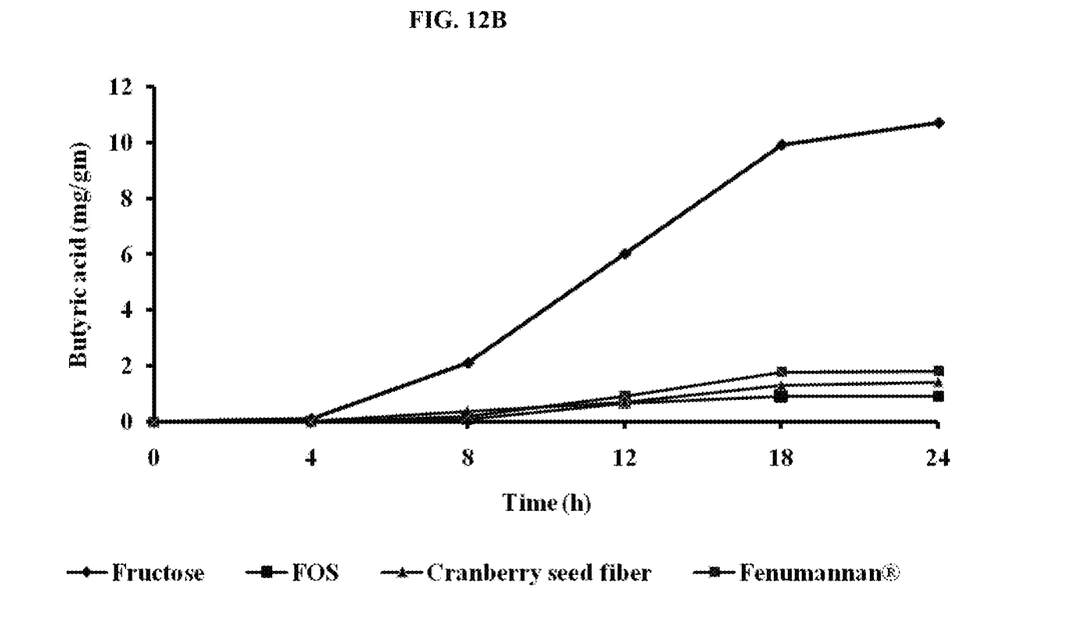
Figure 12C:
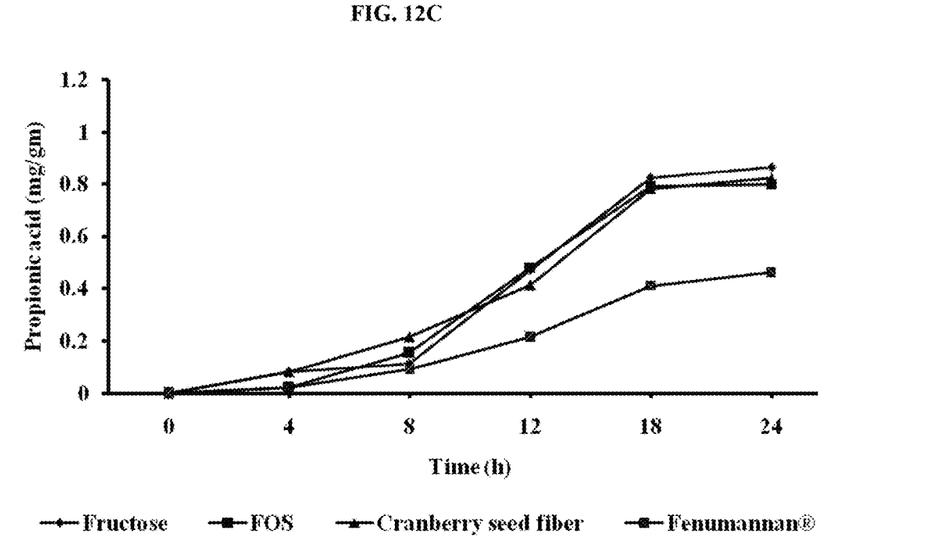

Data represent the mean ± SD of three independent experiments performed in triplicate Short Chain Fatty Acid Production The results of the analysis are presented in FIGS. 12A, 12B and 12C. The production of acetic acid was high for *B. coagulans* MTCC 25235 with FOS, followed by fenugreek seed fibers, cranberry fibers and fructose (FIG. 12 A). Similarly, the production of butyric acid was high for *B. coagulans* MTCC 25235 with fructose, followed by FOS, fenugreek seed fibers and cranberry fibers (FIG. 12 B). The production of propionic acid was similar for *B. coagulans* MTCC 25235 cultured with fructose, FOS and cranberry seed fibers and lower for fenugreek seed fibers (FIG. 12 C).

Storage and Viability

Figure 13:
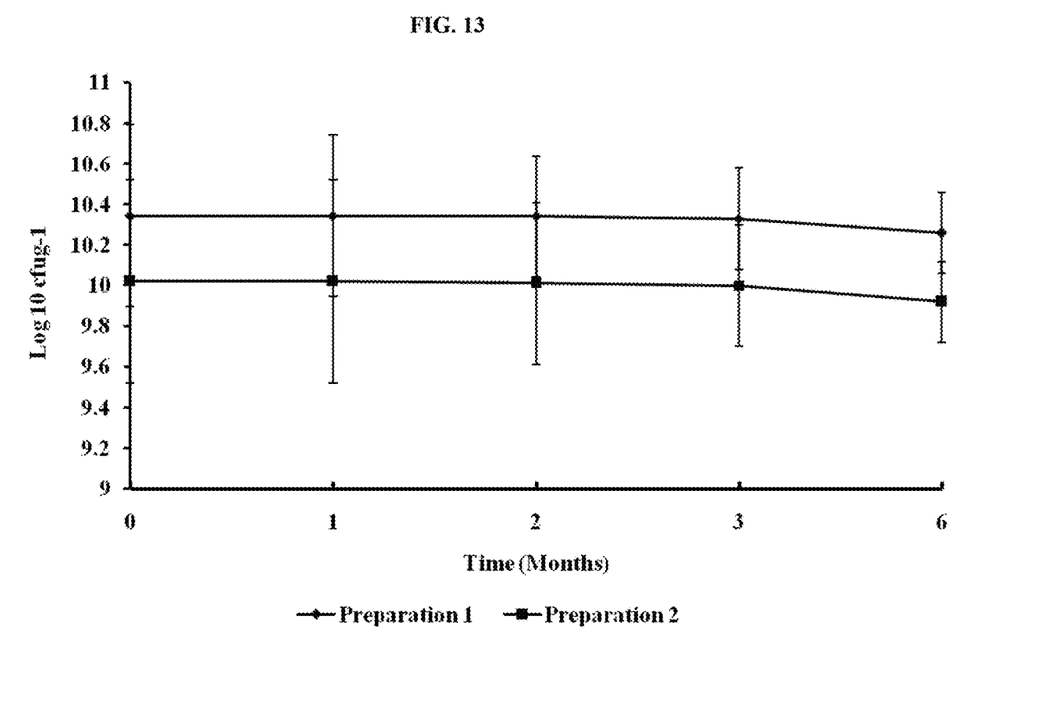
FIG. 13 shows graphical presentation of Viability of *B. coagulans* MTCC 25235 during the storage at temperature 40±2° C. with RH 60%±5%. Two standardized preparations equivalent to $15 \times 10^9$ (preparation 1) and $6 \times 10^9$ cfu/g (preparation 2) were studied. Average means of spore viable counts are expressed in log 10 cfu/g. Each time point represents the mean $Log_{10}$ standard deviations (±SD) of three different experiments performed in duplicate.

Two standardized preparations equivalent to $15 \times 10^9$ (preparation 1) and $6 \times 10^9$ cfu/g (preparation 2) were studied. *B. coagulans* MTCC 25235 showed enhanced viability during the storage at temperature 40±2° C. with RH 60%±5% (FIG. 13)

Example 3: Compositions/Formulations Containing *Bacillus coagulans*

The fructophilic probiotic bacteria can be in the form of an inoculum, freeze-dried powder, fine powder, tablet, capsule, suspension, solution, emulsion, gummy, chewable or edible foods and administered along with accepted excipients, adjuvants, bioavailability enhancers as a stand-alone or in combination with foods rich in fructose selected from the group comprising high fructose corn syrup, honey, Agave, Maple syrup, Coconut sugar, Palm sugar, Molasses, Soda, Candies, sweetened yogurt, frozen foods, canned foods, cereals, fruit juices, coffee creamer, jams and jellies, energy drinks, condiments, ice cream.

In another related aspect, one or more anti-oxidants and anti-inflammatory agents are selected from the group consisting of, but not limited to, vitamin A, D, E, K, C, B complex, rosmarinic acid, Alpha Lipoic Acid, oxyresveratrol, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

In a related aspect the bioavailability enhancer is selected from the group of piperine (BioPerine®), quercetin, garlic extract, ginger extract, and naringin. In another related aspect, the stabilizing agent is selected from the group consisting rosmarinic acid, butylated hydroxyanisole, butylated hydroxytoluene, sodium metabisulfite, propyl gallate, cysteine, ascorbic acid and tocopherols.

In yet another related aspect, the dispersible gums are selected from the group consisting of Agar, Alginate, Carrageenan, Gum Arabic, Guar Gum, Locust Bean Gum, Konjac Gum, Xanthan Gum and Pectin.

Tables 5-9, provide illustrative examples of formulations containing *Bacillus coagulans*

TABLE 5

*Bacillus coagulans* Tablet

Active Ingredients

*Bacillus coagulans* MTCC 25235: 2 billion cfu
Plant fiber
Excipients

Microcrystalline cellulose, Colloidal silicon dioxide, Magnesium stearate

TABLE 6

*Bacillus coagulans* Tablet

Active Ingredients

*Bacillus coagulans* MTCC 25235: 2 billion cfu
Plant fiber
Simethicone
Excipients Microcrystalline cellulose, Colloidal silicon dioxide, Magnesium stearate

TABLE 7

Bacillus coagulans Capsule

| Active Ingredients |
| --- |
| Bacillus coagulans MTCC 25235: 2 billion cfu<br>Plant fiber<br>Excipients |
| Microcrystalline cellulose |

TABLE 8

Bacillus coagulans Capsule

| Active Ingredients |
| --- |
| Bacillus coagulans MTCC 25235: 2 billion cfu<br>Plant fiber<br>Simethicone<br>Excipients |
| Microcrystalline cellulose |

TABLE 9

Bacillus coagulans Powder

| Active Ingredients |
| --- |
| Bacillus coagulans MTCC 25235: 2 billion cfu<br>Plant fiber<br>Excipients |
| Sodium bicarbonate, citric acid, tartaric acid, Polyvinyl pyrrolidone K-30/ Hydroxypropyl Cellulose, Lactose/Mannitol, Sucralose/Sodium Saccharin/ Aspartame, Flavouring agents, Colouring agents |

The above formulations are just illustrative examples, any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A fructophilic probiotic bacteria *Bacillus coagulans* MTCC 25235, isolated from honey, wherein the said bacteria is present in the form of an inoculum, freeze-dried powder, fine powder, tablet, capsule, suspension, solution, emulsion, gummy, chewable or edible foods and administered along with accepted excipients, adjuvants, bioavailability enhancers.

2. The fructophilic bacteria as in claim 1, wherein the said bacteria are isolated from honey using a process comprising steps of:
   a) Mixing honey with saline in the ratio of 1:10 w/v to obtain a suspension;
   b) Thoroughly mixing the suspension of step a) and providing heat shock at 50-70° C. for 30 minutes for selective isolation of spores;
   c) Isolating the bacterial colonies by incubating 1-2 ml of the suspension from step b) in suitable culture media containing fructose for 48 hrs at 35-37° C.;
   d) Purifying bacterial isolates by selecting and incubating morphologically distinct colonies in a suitable media containing fructose as carbon source;
   e) Identifying the bacterial strain by biochemical analysis and 16S rRNA sequencing as *Bacillus coagulans* strain FF7 bearing accession no. MTCC 25235.

3. The method fructophilic bacteria as in claim 2, wherein the honey is selected from the group consisting of, raw honey, filtered honey, acacia honey, alfalfa honey, aster honey, avocado honey, basswood honey, beechwood honey, blueberry honey, bluegum honey, buckwheat honey, clover honey, dandelion honey, eucalyptus honey, fireweed honey, heather honey, ironbark honey, jarrah honey, leatherwood honey, linden honey, macadamia honey, manuka honey, orangeblossom honey, pinetree honey, sourwood honey, sage honey, and tupelo honey.

4. The fructophilic bacteria as in claim 2, wherein the culture media is selected from the group consisting of MRS (De Man, Rogosa and Sharpe agar), GYA (Glucose Yeast Extract Agar), TSB (Tryptone Soya Broth), Sporulation media and Mueller Hinton Agar.

5. The fructophilic bacteria as in claim 2, wherein the isolated probiotic strain returns positive for biochemical tests catalase, oxidase, methyl red, voges proskauers, lactose, xylose, maltose, fructose, dextrose, galactose, raffinose, trehalose, melobiose, sucrose, arabinose, mannose, inulin, sodium gluconate, salicin, sorbitol, mannitol, arabitol, methyl glucoside, rhamnose, cellobiose, ONPG, esculin hydrolysis and negative for biochemical tests sorbose malonate utilization, citrate utilization, xylitol, methyl mannoside, melezitose, erythritol, adonitol, inositol, dulcitol, glycerol, blood hemolysis, citrate and indole.

6. The fructophilic bacteria as claim 1, wherein the optimum pH and temperature for the growth of fructophilic bacteria is 7.5 and 40° C. respectively.

7. The probiotic bacteria as claimed in claim 1, wherein the said fructophilic probiotic bacteria is bile tolerant, gastric acid resistance and produces lactic acid.

\* \* \* \* \*

SEQUENCE LISTING

```
<160> NUMBER OF SEQ ID NOS: 1

<210> SEQ ID NO 1
<211> LENGTH: 1437
<212> TYPE: DNA
<213> ORGANISM: Bacillus coagulans

<400> SEQUENCE: 1
acttgcaagt cgtgcggccc ttttttaaaa gcttgctttt taaaaggtta gcggcggacg      60
ggtgagtaac acgtgggcac cctgcctgta agatcgggat aacgccggga aaccggggct     120
aataccggat agttttttcc tccgcatgga ggaaaaagga aagacggctt ctgctgtcac     180
ttacagatgg gcccgcggcg cattagctag ttggtggggt aacggctcac caaggcaacg     240
atgcgtagcc gacctgagag ggtgatcggc cacattggga ctgagacacg gcccaaactc     300
ctacgggagg cagcagtagg gaatcttccg caatggacga agtctgacg gagcaacgcc      360 gcgtgagtga agaaggcctt cgggtcgtaa aactctgttg ccggggaaga acaagtgccg     420
ttcgaacagg gcggcgcctt gacggtaccc ggccagaaag ccacggctaa ctacgtgcca     480
gcagccgcgg taatacgtag gtggcaagcg ttgtccggaa ttattgggcg taaagcgcgc     540
gcaggcggct tcttaagtct gatgtgaaat ctttgcgggc tcacccgcaa gcggtcattg     600
gaaactggga gggctttgag tgcaagaaag aggagagtgg aatttccacg tgtagcggtg     660
aaatgcgtaa agatgtggag gaacaccagt ggcgaaggcg ctctctggt ctgtaactga      720 cgctgaggcg cgaaagcgtg gggagcaaac aggattagat accctggtag tccacgccgt     780
aaacgatgag tgctaagtgt tagagggttt ccgcccttta gtgctgcagc taacgcatta     840
agcactccgc ctggggagta cggccgcaag gctgaaactc aaaggaattg acggggccc      900 gcacaagcgg tggagcatgt ggtttaattc gaagcaacgc gaagaacctt accaggtctt     960
gacatcctct gacctccctg agacagggc cttcccttc gggggacaga gtgacaggtg      1020
gtgcatggtt gtcgtcagct cgtgtcgtga gatgttgggt taagtcccgc aacgagcgca    1080
acccttgacc ttagttgcca gcattcagtt gggcactcta aggtgactgc cggtgacaaa    1140
ccggaggaag gtggggatga cgtcaaatca tcatgcccct tatgacctgg gctacacacg    1200
```

```
tgctacaatg gatggtacaa agggctgcga gaccgcgagg ttaagccaat cccagaaaac    1260
cattcccagt tcggattgca ggctgcaacc cgcctgcatg aagccggaat cgctagtaat    1320
cgcggatcag catgccgcgg tgaatacgtt cccgggcctt gtacacaccg cccgtcacac    1380
cacgagagtt tgtaacaccc gaagtcggtg aggtaacctt acggagccag ccgccga       1437
```